(12) United States Patent
Cheng

(10) Patent No.: US 8,152,718 B2
(45) Date of Patent: Apr. 10, 2012

(54) MEDICAL DEVICE LIGHT SOURCE

(75) Inventor: Eric Cheng, Bloomington, IN (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 1379 days.

(21) Appl. No.: 11/648,619

(22) Filed: Jan. 3, 2007

(65) Prior Publication Data

US 2007/0185386 A1 Aug. 9, 2007

Related U.S. Application Data

(60) Provisional application No. 60/765,735, filed on Feb. 7, 2006.

(51) Int. Cl.
*A61B 1/06* (2006.01)

(52) U.S. Cl. ........ 600/178; 600/179; 600/182; 362/572; 362/574

(58) Field of Classification Search .............. 600/160, 600/170, 171, 173, 176–179, 182, 476; 362/572, 362/574

See application file for complete search history.

(56) References Cited

U.S. PATENT DOCUMENTS

| | | | |
|---|---|---|---|
| 4,769,292 A | 9/1988 | Tang | |
| 5,315,129 A | 5/1994 | Forrest et al. | |
| 5,554,220 A | 9/1996 | Forrest et al. | |
| 5,642,736 A | 7/1997 | Avitall | |
| 5,703,436 A | 12/1997 | Forrest et al. | |
| 5,707,745 A | 1/1998 | Forrest et al. | |
| 5,721,160 A | 2/1998 | Forrest et al. | |
| 5,757,026 A | 5/1998 | Forrest et al. | |
| 5,757,139 A | 5/1998 | Forrest et al. | |
| 5,811,833 A | 9/1998 | Thompson | |
| 5,834,893 A | 11/1998 | Bulovic et al. | |
| 5,844,363 A | 12/1998 | Gu et al. | |
| 5,861,219 A | 1/1999 | Thompson et al. | |
| 5,871,469 A | 2/1999 | Eggers et al. | |
| 5,874,803 A | 2/1999 | Garbuzov et al. | |
| 5,904,147 A | 5/1999 | Conlan | |
| 5,917,280 A | 6/1999 | Burrows et al. | |
| 5,922,396 A | 7/1999 | Thompson | |

(Continued)

FOREIGN PATENT DOCUMENTS

DE 21 52 773 A1 4/1972

(Continued)

OTHER PUBLICATIONS

International Search Report from PCT/US2007/000040 mailed Oct. 1, 2007 (4 pages).

(Continued)

*Primary Examiner* — John P Leubecker
*Assistant Examiner* — Samuel Candler
(74) *Attorney, Agent, or Firm* — Finnegan, Henderson, Farabow, Garrett & Dunner LLP

(57) ABSTRACT

Embodiments of the invention are directed medical devices for illuminating and viewing a patient's internal body portion. The device may include an elongated flexible tube including a distal end and a proximal end. The tube defines a channel extending from the proximal end to an aperture at the distal end. An illumination device is housed within the channel and configured to emit a distally directed path of light. A light source is provided at the distal end of the flexible tube and configured to emit a laterally directed path of light. In one embodiment the light source is a organic light emitting diode.

20 Claims, 3 Drawing Sheets

U.S. PATENT DOCUMENTS

| | | |
|---|---|---|
| 5,932,895 A | 8/1999 | Shen et al. |
| 5,953,587 A | 9/1999 | Forrest et al. |
| 5,981,306 A | 11/1999 | Burrows et al. |
| 5,986,268 A | 11/1999 | Forrest et al. |
| 5,986,401 A | 11/1999 | Thompson et al. |
| 5,998,803 A | 12/1999 | Forrest et al. |
| 6,005,252 A | 12/1999 | Forrest et al. |
| 6,013,538 A | 1/2000 | Burrows et al. |
| 6,013,982 A | 1/2000 | Thompson et al. |
| 6,030,700 A | 2/2000 | Forrest et al. |
| 6,030,715 A | 2/2000 | Thompson et al. |
| 6,045,930 A | 4/2000 | Thompson et al. |
| 6,046,543 A | 4/2000 | Bulovic et al. |
| 6,048,630 A | 4/2000 | Burrows et al. |
| 6,087,196 A | 7/2000 | Sturm et al. |
| 6,091,195 A | 7/2000 | Forrest et al. |
| 6,097,147 A | 8/2000 | Baldo et al. |
| 6,111,902 A | 8/2000 | Kozlov et al. |
| 6,124,046 A | 9/2000 | Jin |
| 6,125,226 A | 9/2000 | Forrest et al. |
| 6,127,693 A | 10/2000 | Chen |
| 6,143,814 A | 11/2000 | Schiller et al. |
| 6,150,043 A | 11/2000 | Thompson et al. |
| 6,166,489 A | 12/2000 | Thompson et al. |
| 6,185,443 B1 | 2/2001 | Crowley |
| 6,210,814 B1 | 4/2001 | Thompson et al. |
| 6,214,631 B1 | 4/2001 | Burrows et al. |
| 6,232,714 B1 | 5/2001 | Shen et al. |
| 6,242,115 B1 | 6/2001 | Thomson et al. |
| 6,245,393 B1 | 6/2001 | Thompson et al. |
| 6,259,202 B1 | 7/2001 | Sturm et al. |
| 6,261,226 B1 * | 7/2001 | McKenna et al. ............. 600/109 |
| 6,264,805 B1 | 7/2001 | Forrest et al. |
| 6,274,980 B1 | 8/2001 | Burrows et al. |
| 6,287,712 B1 | 9/2001 | Bulovic et al. |
| 6,294,398 B1 | 9/2001 | Kim et al. |
| 6,297,516 B1 * | 10/2001 | Forrest et al. .................. 257/40 |
| 6,300,756 B2 | 10/2001 | Sturm et al. |
| 6,303,238 B1 | 10/2001 | Thompson et al. |
| 6,310,360 B1 | 10/2001 | Forrest et al. |
| 6,312,836 B1 | 11/2001 | Bulovic et al. |
| 6,329,085 B1 | 12/2001 | Burrows et al. |
| 6,330,262 B1 | 12/2001 | Burrows et al. |
| 6,331,156 B1 | 12/2001 | Haefele et al. |
| 6,331,438 B1 | 12/2001 | Aylott |
| 6,333,521 B1 | 12/2001 | Thompson et al. |
| 6,337,102 B1 | 1/2002 | Forrest et al. |
| 6,350,875 B1 | 2/2002 | Weber et al. |
| 6,358,631 B1 | 3/2002 | Forrest et al. |
| 6,365,270 B2 | 4/2002 | Forrest et al. |
| 6,366,268 B1 | 4/2002 | Forrest et al. |
| 6,387,544 B1 | 5/2002 | Thompson et al. |
| 6,396,860 B1 | 5/2002 | Kozlov et al. |
| 6,403,392 B1 | 6/2002 | Burrows et al. |
| 6,413,656 B1 | 7/2002 | Thompson et al. |
| 6,420,031 B1 | 7/2002 | Parthasarathy et al. |
| 6,449,006 B1 | 9/2002 | Shipp |
| 6,495,198 B2 | 12/2002 | Peng |
| 6,551,240 B2 | 4/2003 | Henzler |
| 6,579,629 B1 | 6/2003 | Raychaudhuri |
| 6,613,002 B1 | 9/2003 | Clark |
| 6,620,497 B2 | 9/2003 | Smith |
| 6,627,333 B2 | 9/2003 | Hatwar |
| 6,730,019 B2 | 5/2004 | Irion |
| 6,814,699 B2 | 11/2004 | Ross et al. |
| 6,951,536 B2 * | 10/2005 | Yokoi et al. ................... 600/128 |
| 6,964,501 B2 | 11/2005 | Ryan |
| 7,553,276 B2 * | 6/2009 | Iddan ............................ 600/160 |
| 2002/0038121 A1 | 3/2002 | Rozenberg |
| 2002/0120181 A1 | 8/2002 | Irion |
| 2002/0193664 A1 | 12/2002 | Ross |
| 2003/0036031 A1 | 2/2003 | Lieb et al. |
| 2003/0095781 A1 | 5/2003 | Williams |
| 2003/0125719 A1 | 7/2003 | Furnish |
| 2004/0111132 A1 | 6/2004 | Shenderova |
| 2004/0196222 A1 | 10/2004 | Shih et al. |
| 2005/0043586 A1 | 2/2005 | Suzushima |
| 2005/0106710 A1 * | 5/2005 | Friedman et al. .......... 435/287.1 |
| 2005/0137459 A1 | 6/2005 | Chin |
| 2006/0069313 A1 * | 3/2006 | Couvillon et al. ............ 600/179 |
| 2006/0098203 A1 | 5/2006 | Kalveram |

FOREIGN PATENT DOCUMENTS

| | | |
|---|---|---|
| GB | 2 356 464 A | 5/2001 |
| GB | 2356464 A | 5/2001 |
| GB | 2 408 209 A | 5/2005 |
| WO | WO 98/01412 | 1/1998 |
| WO | WO 98/34214 A1 | 8/1998 |
| WO | WO 03/019073 A1 | 3/2003 |
| WO | WO 03/075979 A2 | 9/2003 |
| WO | WO 2004/048881 A2 | 6/2004 |

OTHER PUBLICATIONS

"Heat Transfer and Thermal Conductivity Are Not Linearly Related," Cool Polymers® Technical Bulletin, Insight on the use of thermally conductive plastics, vol. 1, No. 2, 2002, (4 pages).

"SOLED Stacked Organic Light Emitting Device," Universal Display Corporation, Technology, Feb. 2001, (3 pages).

* cited by examiner

MEDICAL DEVICE LIGHT SOURCE

CROSS REFERENCE TO RELATED APPLICATIONS

This application claims the benefit of U.S. Provisional Application No. 60/765,735, filed Feb. 7, 2006, under 35 U.S.C. §119(e). The entire disclosure of that provisional application is incorporated by reference herein.

FIELD OF THE INVENTION

This invention relates to an illumination system in a medical device and a system to assist in viewing an internal treatment location of a patient during a medical procedure. More particularly, embodiments of the invention relate to devices and methods for lighting and viewing internal treatment portions within a patient's body, such as, for example, within anatomical lumens of the body or within a solid tissue mass, during insertion and movement of a device during a medical procedure.

BACKGROUND OF THE INVENTION

Endoscopes for medical use have been adopted for various diagnostic and medical treatment procedures. Endoscopes have been used for the diagnosis and treatment of a wide range of diseases and disorders that often require a physician to access the tortuous and relatively small cross-sectional areas of a patient's internal anatomical body lumens. A patient's pancreaticobiliary system (including the anatomical regions of the gall bladder, pancreas, and the biliary tree), for example, is accessed for diagnosis and/or treatment of disorders of certain portions of the digestive system.

As another example, endoscopes are used with immobilization and retrieval devices for stabilizing and/or removing organic material (e.g., blood clots, tissue, and biological concretions such as urinary, biliary, and pancreatic stones) and inorganic material (e.g., components of a medical device or other foreign matter), which may obstruct or otherwise be present within a body's anatomical lumens. For example, concretions can develop in certain parts of the body, such as in the kidneys, pancreas, and gallbladder. Minimally invasive medical procedures generally involve causing limited trauma to the tissues of a patient and can be used to dispose of problematic concretions. Lithotripsy and ureteroscopy, for example, are used to view and treat urinary calculi (e.g., kidney stones) in the ureter of patients.

One of the most common methods for non-invasively viewing an internal body cavity of a patient is with an imaging endoscope. Such endoscopes are elongated devices that are inserted into the body cavity. Light is delivered through an illumination channel of the endoscope, and reflected light is gathered by one or more lenses that are coupled to an imaging channel. Light from the imaging channel is transmitted out of the endoscope and supplied to a camera or other viewing device so that a physician can examine the internal body tissue.

The internal body portions accessed by an endoscope, however, are remote from atmospheric light. This poor lighting (or even absence of light) within a target treatment portion requires that an endoscope be equipped with an internal light source. Known endoscope systems use an external light source transmitted to the treatment area through an optical fiber, for example. Other known systems present multiple optical fibers in a bundle to provide light at the tip of an endoscope. Such optical fiber light sources present a narrow beam of light illuminating an area directly incident to the path of the light rays emitted from the fibers. In endoscopes having, for example, front/forward directed light sources, the lighting is often ineffective since the only illuminated area is the narrow path directly incident to the direction of the emitted light rays. This arrangement is equated to using a flashlight in a dark cave. Accordingly, there is a need for a supplemental endoscope light source for illuminating a greater area of a treatment location of a patient.

FIG. 1, for example, illustrates a known endoscope system. For purposes of this disclosure, "distal" refers to the end further from the device operator during use and "proximal" refers to the end closer to the device operator during use. FIG. 1 depicts a known endoscope 10 including a flexible outer tube 12 extending between a distal end 14 and a proximal end (not shown) of the device. The distal end 14 of endoscope 10 is illustrated as positioned within a patient's internal body portion, such as, for example, anatomical lumen 18. The endoscope 10 includes an illumination channel 15 housing at least one optical fiber 16 therein.

As seen in FIG. 1, optical fiber 16 emits a distally directed path of light comprising an illumination path 20. As seen in FIG. 1, only the area upon which illumination path 20 impinges is illuminated and therefore viewable by an operator. Therefore, in the illustrated arrangement, only the area in the direct forward path of the endoscope 10 is illuminated for viewing. An area depicted by arrows 22 represents a portion of lumen 18, extending laterally beyond, and proximal away from, the illumination path 20. Accordingly, arrows 22 depict a dark, poorly lit portion of lumen 18. As a result of the relatively narrow area lighted by illumination path 20, only a small forwardly directed portion of lumen 18 is viewable by the operator.

The optical fiber 16 extends within an illumination channel 15 of the endoscope for emitting light at the treatment region of an endoscope. In use, optical fibers and their housing lumens occupy a portion of the available area of the endoscope. An alternative light source could eliminate the need for optical fibers and illumination channels, thereby decreasing the outer diameter of the endoscope. Accordingly, there is a need for an improved alternative endoscope light source that overcomes the disadvantages of optical fibers and provides a reduced size for a combined medical device and light source.

SUMMARY OF THE INVENTION

Embodiments of the present invention are directed to a medical device and illumination system that obviates one or more of the limitations and disadvantages of prior medical devices.

In one embodiment, the medical device includes an elongated flexible tube including a distal end and a proximal end. The tube defines a channel extending from the proximal end to an aperture at the distal end. An illumination device is housed within the channel and configured to emit a distally directed path of light. A light source is provided at the distal end of the flexible tube and configured to emit a laterally directed path of light.

In various embodiments, the medical device may include one or more of the following additional features: wherein the flexible tube defines a longitudinal axis extending between the distal and proximal ends of the flexible tube, the distally directed path of light extends substantially parallel to the longitudinal axis of the flexible tube, and the laterally directed path of light extends substantially perpendicular to the longitudinal axis of the flexible tube; wherein the light source is provided along an outside surface of the flexible tube along a distal end of the flexible tube; wherein the light source is a coating; wherein the light source completely surrounds the outside surface of the flexible tube along the distal end; wherein the light source is a flexible organic light emitting diode (FOLED); wherein the light source is provided on a flexible base material comprising one of polyethylene terephthalate (PET), polyethylene naphthalate (PEN), or a reflective metal foil; wherein the light source is one of a transparent organic light emitting diode (TOLED), a phosphorescent organic light emitting diode (PHOLED), and a stacked organic light emitting diode (SOLED); wherein the light source comprises a combination of two or more of (1) a transparent organic light emitting diode (TOLED), (2) a phosphorescent organic light emitting diode (PHOLED), (3) a flexible organic light emitting diode (FOLED), and (4) a stacked organic light emitting diode (SOLED); wherein the light source comprises a thin film including silver molecules to which electric current is applied to derive electroluminescence therefrom; wherein the light source is configured to emit a distally directed path of light; and wherein the light source is provided along a distal facing surface of the flexible tube; wherein the illumination device comprises at least one optical fiber; wherein power is supplied to the light source through electrical wiring housed within the medical device; and wherein power is supplied to the light source through a magnetic field generated external to a patient and an induction coil on the medical device.

Another embodiment of the invention is directed to a medical device including an elongated flexible tube including a distal end and a proximal end. The tube defines a channel extending from the proximal end to an aperture at the distal end. A light source is provided along an outside surface of the flexible tube at a distal end of the flexible tube and is configured to emit light laterally and distally of the distal end of the flexible tube.

In various embodiments, the medical device may include one or more of the following additional features: wherein the flexible tube defines a longitudinal axis extending between the distal and proximal ends of the flexible tube, the distally directed path of light extends substantially parallel to the longitudinal axis of the flexible tube, and the laterally directed path of light extends substantially perpendicular to the longitudinal axis of the flexible tube; wherein the light source is a coating; wherein the light source completely surrounds the outside surface of the flexible tube along the distal end; further comprising an illumination device housed within the channel configured to emit a distally directed path of light; wherein the light source is a flexible organic light emitting diode (FOLED); wherein the light source is provided on a flexible base material comprising one of polyethylene terephthalate (PET), polyethylene naphthalate (PEN), or a reflective metal foil; wherein the light source is one of a transparent organic light emitting diode (TOLED), a phosphorescent organic light emitting diode (PHOLED), and a stacked organic light emitting diode (SOLED); wherein the light source comprises a combination of two or more of (1) a transparent organic light emitting diode (TOLED), (2) a phosphorescent organic light emitting diode (PHOLED), (3) a flexible organic light emitting diode (FOLED), and (4) a stacked organic light emitting diode (SOLED); wherein the light source comprises a thin film including silver molecules to which electric current is applied to derive electroluminescence therefrom; wherein the light source is provided along a distal facing surface of the flexible tube; wherein the illumination device comprises at least one optical fiber; wherein the outside surface includes a distal facing surface of the flexible tube; wherein the channel is configured to receive a treatment instrument; wherein power is supplied to the light source through electrical wiring housed within the medical device; and wherein power is supplied to the light source through a magnetic field generated external to a patient and an induction coil on the medical device.

Additional objects and advantages of the invention will be set forth in part in the description which follows, and in part will be obvious from the description, or may be learned by practice of the invention. The objects and advantages of the invention will be realized and attained by means of the elements and combinations particularly pointed out in the appended claims.

It is to be understood that both the foregoing general description and the following detailed description are exemplary and explanatory only and are not restrictive of the invention, as claimed.

BRIEF DESCRIPTION OF THE DRAWINGS

The accompanying drawings, which are incorporated in and constitute a part of this specification, illustrate several embodiments of the invention and together with the description, serve to explain the principles of the invention.

DESCRIPTION OF THE EMBODIMENTS

Figure 1:
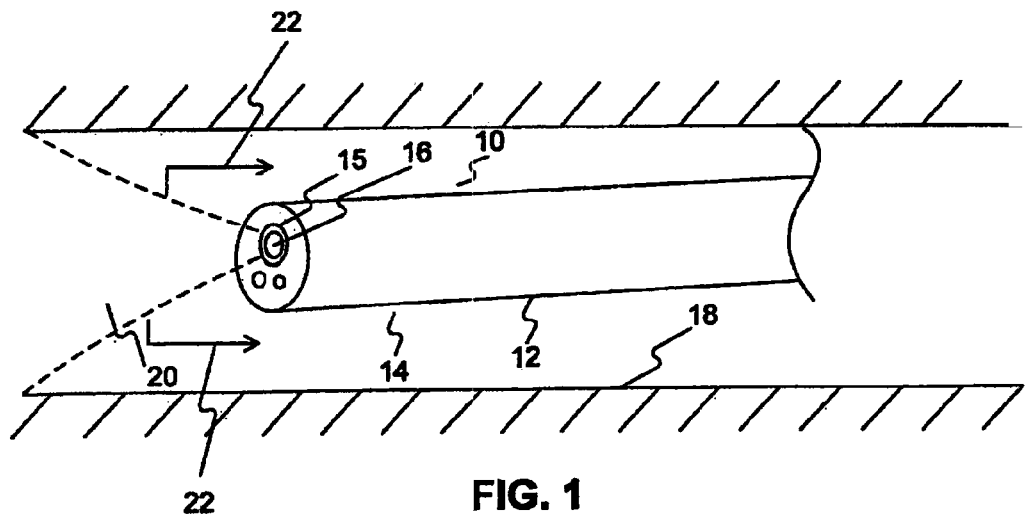
FIG. 1 is a side view illustrating a distal portion of a known imaging endoscope within an internal body portion.

Reference will now be made in detail to the exemplary embodiments of the invention, examples of which are illustrated in the accompanying drawings. Wherever possible, the same reference numbers will be used throughout the drawings to refer to the same or like parts. The drawing figures of this application are intended to provide a general understanding of the working elements of the underlying system. Accordingly, unless explicitly stated, the figures do not represent a literal depiction of proportional dimensions or the precise locations for the illustrated inter-related components.

According to exemplary embodiments, the invention relates to a medical device and illumination system for viewing a patient's internal body portion. In some embodiments, the medical device includes an internal working channel that receives a treatment device in an endoscopic medical procedure. The treatment device can be advanced through a working channel of an endoscope, including an endoscope specifically designed and/or sized for use with the treatment device, and into a tissue tract. For purposes of this disclosure, "treatment device" or "treatment instrument" includes, for example, any medical device advanced through a working channel of an endoscope and for use during an endoscopic procedure. Exemplary treatment instruments include, but are not limited to, guide wires, cutting or grasping forceps, biopsy devices, snare loops, injection needles, cutting blades, scissors, retractable baskets, retrieval devices, ablation and/or electrophysiology catheters, stent placement devices, surgical stapling devices, and balloon catheters.

Figure 2:
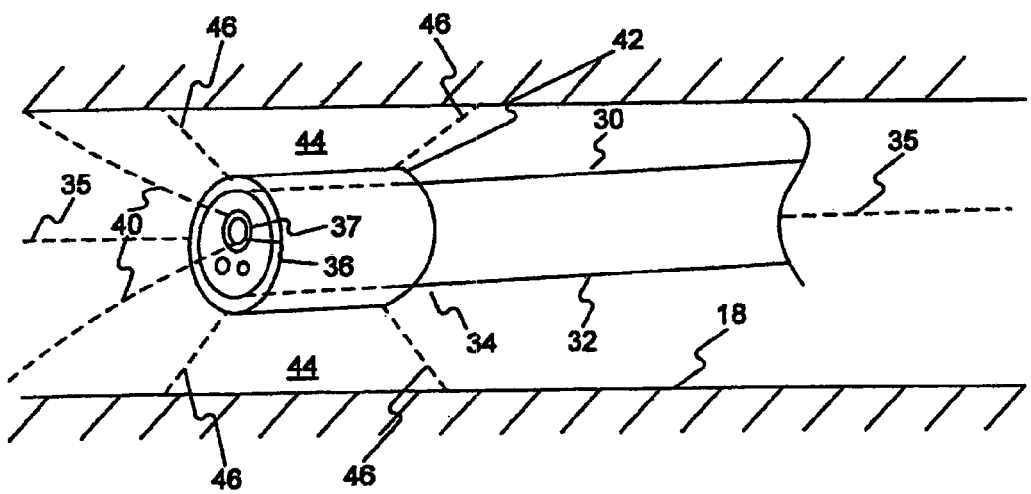
FIG. 2 is a side view illustrating a distal portion of a medical device including a supplemental light source, according to an embodiment of the invention.

FIG. 2 is a side view illustrating a distal portion of a medical device, according to an embodiment of the invention.

FIG. 2 depicts an endoscope 30 including a flexible outer tube 32 extending between a distal end 34 and a proximal end (not shown) of the device. The flexible outer tube 32 extends along a longitudinal axis 35. The distal end 34 of endoscope 30 is illustrated as positioned within a patient's internal body portion, such as, for example, anatomical lumen 18. The endoscope 30 includes an illumination channel 37 housing at least one optical fiber 36 therein.

Optical fiber 36 emits a distally directed path of light comprising a forwardly directed illumination path 40 extending substantially parallel to the longitudinal axis 35. Illumination path 40 lights the area in the direct forward path of the endoscope 40 for viewing by an operator. Endoscope 30 further includes a supplemental light source 42 provided along an outside surface of tube 32 at the distal end of endoscope 30. In one embodiment, supplemental light source 42 emits light away from the distal portion of flexible tube 32. For example, supplemental light source 42 may emit light away from tube 32 in directions substantially perpendicular to the longitudinal axis 35, otherwise orthogonal to axis 35, or even along axis 35. In one embodiment, as seen in FIG. 2, light source 42 can be configured to emit a laterally directed path of light comprising a laterally directed peripheral illumination zone 44, shown bounded by dashed lines 46. In other embodiments, light source 42 can be configured to emit light in all directions and angles relative to axis 35.

As seen in FIG. 2, the addition of supplemental light source 42 expands the illuminated portion of the working field within a desired treatment portion of lumen 18. The combined illumination of forwardly directed path 40 and peripherally directed zone 44 provides an operator with an expanded view of the working field. This expanded view in turn provides a larger and clearer image to an operator, thereby improving the accuracy with which an operator can position the underlying endoscope or use a treatment device passed through a working channel of the endoscope. In addition, this expanded view and increased accuracy can reduce the length of time required for a particular diagnostic/treatment procedure and reduce instances of tissue trauma resulting from improper or prolonged endoscope positioning or treatment device use.

Light source 42 can be comprised of a relatively flexible and thin material configured for incorporation along the distal end of an endoscope. One exemplary light source is an organic light emitting diode (OLED). OLEDs have been constructed using rigid, glass based materials for a supporting structure. In order to protect such OLEDs from the corrupting effects of water and oxygen, OLEDs can be sealed with glass or metal using an ultraviolet-cured epoxy resin. Such configurations, however, can result in a relatively bulky and rigid light source, thereby adding to an overall profile of the underlying endoscope.

A more preferred exemplary light source therefore is a flexible organic light emitting diode (FOLED). A FOLED comprises light emitting diode structure constructed using a flexible base material, such as clear plastic film or reflective metal foil. FOLEDs can comprise a relatively light-weight, thin, flexible, and durable light source manufactured on a variety of substrates having such characteristics. Exemplary materials for the underlying base substrate of a FOLED include, but are not limited to, thin plastics, such as, for example, polyethylene terephthalate (PET) or polyethylene naphthalate (PEN) polyester-type films. In addition, bendable metallic foils are also contemplated as being potential base materials.

Alternative materials for the light source will include any materials that are sufficiently thin to be applied on the outer surface of the scope and contain electroluminescent properties. For example, another exemplary light source involves deriving electroluminescence from individual molecules by exposing the molecules (such as molecules including silver or copper, for example) to electrical current, which results in the production of light through the emission of photons. (See, for example, the light sources described at http://gtresearchnews.gatech.edu/newsrelease/NANOLIGHT.htm.) The application of both direct current (DC) and alternating current (AC) has proved to be effective in producing light from sources as small as those in the nanometer-scale within thin films of silver oxide, with the application of alternating current resulting in a greater magnitude.

Other exemplary light sources include, but are not limited to alternative organic LED variations. For example, light source 42 can be comprised of materials such as TOLEDs (transparent OLEDs), PHOLEDs (phosphorescent OLEDs), and SOLEDs (stacked OLEDs) from Universal Display Corporation of Ewing, N.J. Reference is made to www.universaldisplay.com for further information on organic light emitting device technology.

A power supply to the FOLED or other light source may be externally supplied. One way to supply the power is through thin electrical wiring through the underlying endoscope. This power supply is still an advantageous alternative to lighting through optical fibers because the electrical wiring is much thinner and more flexible than a fiber optic bundle. Another way to power the light supply is through wireless induction power. In such a configuration, a magnetic field is generated outside the body and an induction coil on the scope converts the magnetic field into electrical power for use by the light source.

Figure 3:
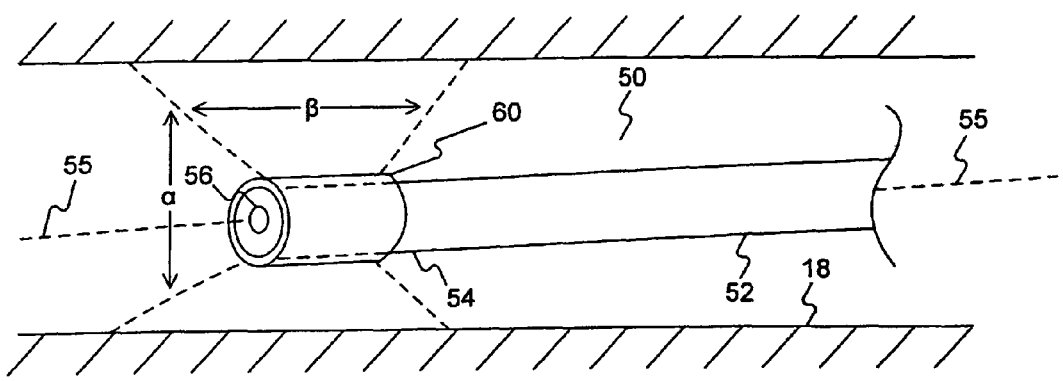
FIG. 3 is a side view illustrating a distal portion of a medical device including a light source, according to an embodiment of the invention.

FIG. 3 is a side view illustrating a distal portion of a medical device including a light source, according to another embodiment of the invention. FIG. 3 depicts an endoscope 50 including a flexible outer tube 52 extending between a distal end 54 and a proximal end (not shown) of the device. The flexible outer tube 52 extends along a longitudinal axis 55. The distal end 54 of endoscope 50 is illustrated as positioned within a patient's internal body portion, such as, for example, anatomical lumen 18. The endoscope 50 includes a light source 60 integrated along a distal tip of the endoscope 50.

A working channel 56 extends through the flexible tube 52 and exits beyond the distal face of endoscope 50, such that a treatment device can access the patient's lumen 18. In one embodiment, light source 60 is provided (or coated, for example, in embodiments using FOLEDs as light source 60) along a distal portion of the outside surface of flexible tube 52 as well as a portion of the distal facing surface of flexible tube 52. In such an arrangement, light source 60 is configured to emit not only a laterally directed path of light, emitted orthogonal to and substantially perpendicular to longitudinal axis 55, but also a forwardly directed path of light, extending along and substantially parallel to the longitudinal axis 55. For example, in the embodiment shown in FIG. 3, the light source 60 can be configured to emit a laterally directed path of light comprising a peripheral illumination zone $\beta$. In addition, as noted above, light source 60 can be configured to emit a distally directed path of light comprising a forwardly directed illumination path $\alpha$. Zones $\alpha$ and $\beta$ essentially form one continuous illuminated area extending substantially completely around the distal tip of endoscope 50. Since light source 60 directs light both peripheral to and forward of the flexible tube 52, the combined illumination provides an operator with an expanded view of the working field.

As noted above with regard to the embodiment of FIG. 2, this expanded view in turn provides a larger and clearer image to an operator, thereby improving the accuracy with which an operator can position the underlying endoscope. In addition to these benefits, the use of light source 60, integrated with the distal end of endoscope 50, allows for the deletion of fiber optic illumination means, thereby reducing the outer diameter necessary for endoscope 50. Furthermore, in embodiments where the light source 60 comprises flexible and relatively thin base materials, such as, for example, FOLED light sources, the flexible thin coating along the distal tip of the endoscope further facilitates the manufacture of a reduced diameter medical device.

In addition to the above described embodiments, alternative light sources can be configured to emit light at angle other that those parallel and perpendicular to a longitudinal axis of a medical device. For example, a medical device may incorporate a light source in accordance with this invention that emits light at various intermediate/oblique angles relative to the longitudinal axis of the medical device. In various alternative embodiments a light source providing an intermediate/oblique light path can be provided in place of, or in addition to, any of the above-described light sources.

Figure 4:
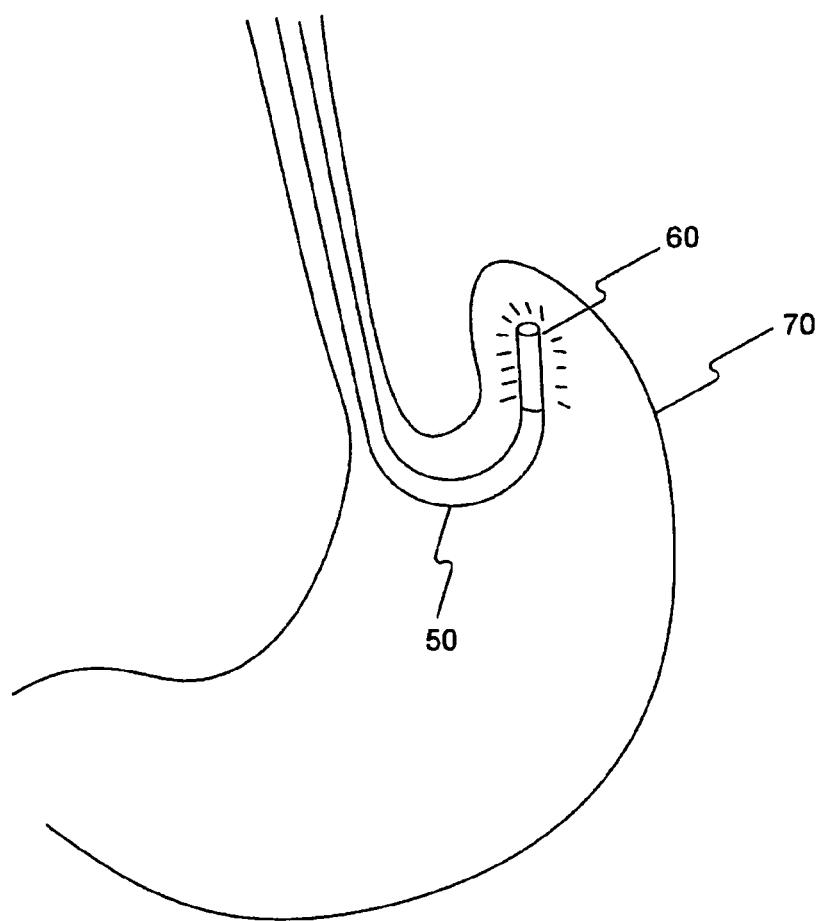
FIG. 4 illustrates a distal portion of a medical device according to an embodiment of the invention deployed within a patient's internal body portion.

FIG. 4 illustrates the positioning of an endoscope 30 or 50 within a patient's body portion. In particular, FIG. 4 depicts the endoscope 50 extended within a patient's stomach 70 such that the integrated light source 60 along a distal tip of the endoscope 50 illuminates the internal cavity of the patient's stomach 70. As illustrated in FIG. 4, the endoscope 50 can be selectively manipulated by an operator such that the distal end of the endoscope is deflected to reach a particular desired internal body portion for examination or treatment. In embodiments where light source 60 is comprised of a FOLED, the endoscope affords the additional benefits of further flexibility, even along the terminal distal portion of endoscope 50 that incorporates light source 60.

While this specification makes reference to endoscope devices, the invention is not intended to be so limited. Accordingly, the elements described in this application may be used with any other medical device requiring, or even benefiting from, a light source. Other embodiments of the invention will be apparent to those skilled in the art from consideration of the specification and practice of the invention disclosed herein. It is intended that the specification and examples be considered as exemplary only, with a true scope and spirit of the invention being indicated by the following claims.

What is claimed is:

1. A medical device, comprising:
   an elongated flexible tube including a distal end and a proximal end, the tube defining a channel extending from the proximal end to an aperture at the distal end;
   an illumination device housed within the channel configured to emit a distally directed path of light; and
   a light source provided at the distal end of the flexible tube configured to emit a laterally directed path of light,
   wherein the light source is a flexible organic light emitting diode (FOLED), and
   wherein the illumination device comprises at least one optical fiber.

2. The medical device of claim 1, wherein the flexible tube defines a longitudinal axis extending between the distal and proximal ends of the flexible tube, the distally directed path of light extends substantially parallel to the longitudinal axis of the flexible tube, and the laterally directed path of light extends substantially perpendicular to the longitudinal axis of the flexible tube.

3. The medical device of claim 1, wherein the light source is provided along an outside surface of the flexible tube along a distal end of the flexible tube.

4. The medical device of claim 3, wherein the light source completely surrounds the outside surface of the flexible tube along the distal end.

5. The medical device of claim 3, wherein the light source is provided along a distal facing surface of the flexible tube.

6. The medical device of claim 1, wherein the light source is provided on a flexible base material comprising one of polyethylene terephthalate (PET), polyethylene naphthalate (PEN), or a reflective metal foil.

7. The medical device of claim 1, wherein the light source comprises a combination of the flexible organic light emitting diode (FOLED) and one of a transparent organic light emitting diode (TOLED), a phosphorescent organic light emitting diode (PHOLED), and a stacked organic light emitting diode (SOLED).

8. The medical device of claim 1, wherein the light source comprises a combination of the flexible organic light emitting diode (FOLED) and two or more of (1) a transparent organic light emitting diode (TOLED), (2) a phosphorescent organic light emitting diode (PHOLED), and (3) a stacked organic light emitting diode (SOLED).

9. The medical device of claim 1, wherein the light source is configured to emit a distally directed path of light.

10. The medical device of claim 1, wherein power is supplied to the light source through electrical wiring housed within the medical device.

11. A medical device, comprising:
    an elongated flexible tube including a distal end and a proximal end, the tube defining a channel extending from the proximal end to an aperture at the distal end;
    a light source provided along an outside surface of the flexible tube at a distal end of the flexible tube, the light source configured to emit light laterally and distally of the distal end of the flexible tube,
    wherein the light source is a flexible organic light emitting diode (FOLED), and
    an illumination device housed within the channel configured to emit a distally directed path of light,
    wherein the illumination device comprises at least one optical fiber.

12. The medical device of claim 11, wherein the flexible tube defines a longitudinal axis extending between the distal and proximal ends of the flexible tube, the distally directed path of light extends substantially parallel to the longitudinal axis of the flexible tube, and the laterally directed path of light extends substantially perpendicular to the longitudinal axis of the flexible tube.

13. The medical device of claim 11, wherein the light source completely surrounds the outside surface of the flexible tube along the distal end.

14. The medical device of claim 11, wherein the light source is provided on a flexible base material comprising one of polyethylene terephthalate (PET), polyethylene naphthalate (PEN), or a reflective metal foil.

15. The medical device of claim 11, wherein the light source comprises a combination of the flexible organic light emitting diode (FOLED) and one of a transparent organic light emitting diode (TOLED), a phosphorescent organic light emitting diode (PHOLED), and a stacked organic light emitting diode (SOLED).

16. The medical device of claim 11, wherein the light source comprises a combination of the flexible organic light emitting diode (FOLED) and two or more of (1) a transparent organic light emitting diode (TOLED), (2) a phosphorescent organic light emitting diode (PHOLED), (FOLED), and (3) a stacked organic light emitting diode (SOLED).

17. The medical device of claim 11, wherein the light source is provided along a distal facing surface of the flexible tube.

18. The medical device of claim 11, wherein the outside surface includes a distal facing surface of the flexible tube.

19. The medical device of claim 11, wherein the channel is configured to receive a treatment instrument.

20. The medical device of claim 11, wherein power is supplied to the light source through electrical wiring housed within the medical device.

* * * * *

UNITED STATES PATENT AND TRADEMARK OFFICE
CERTIFICATE OF CORRECTION

PATENT NO.       : 8,152,718 B2
APPLICATION NO.  : 11/648619
DATED            : April 10, 2012
INVENTOR(S)      : Eric Cheng Page 1 of 1

It is certified that error appears in the above-identified patent and that said Letters Patent is hereby corrected as shown below:

Claim 16, col. 8, line 66,

"organic light emitting diode (PHOLED), (FOLED), and (3) a" should read

--organic light emitting diode (PHOLED), and (3) a--

Signed and Sealed this
Twelfth Day of June, 2012

David J. Kappos
*Director of the United States Patent and Trademark Office*